US010551380B2

(12) United States Patent
Boyle et al.

(10) Patent No.: US 10,551,380 B2
(45) Date of Patent: Feb. 4, 2020

(54) TLR AGONIST-ENHANCED IN VITRO ASSAY OF CELL MEDIATED IMMUNE RESPONSIVENESS

(75) Inventors: Jeff Boyle, Pearcedale (AU); Emily Manktelow, Diamond Creek (AU)

(73) Assignee: Cellestis Limited, Chadstone (AU)

(*) Notice: Subject to any disclaimer, the term of this patent is extended or adjusted under 35 U.S.C. 154(b) by 9 days.

(21) Appl. No.: 14/114,335

(22) PCT Filed: Apr. 20, 2012

(86) PCT No.: PCT/AU2012/000413
§ 371 (c)(1),
(2), (4) Date: Feb. 25, 2014

(87) PCT Pub. No.: WO2012/145786
PCT Pub. Date: Nov. 1, 2012

(65) Prior Publication Data
US 2014/0154712 A1   Jun. 5, 2014

Related U.S. Application Data

(60) Provisional application No. 61/480,913, filed on Apr. 29, 2011.

(51) Int. Cl.
*G01N 33/49* (2006.01)
*G01N 33/569* (2006.01)
*G01N 33/50* (2006.01)

(52) U.S. Cl.
CPC ............... *G01N 33/56972* (2013.01)

(58) Field of Classification Search
None
See application file for complete search history.

(56) References Cited

U.S. PATENT DOCUMENTS

| | | | |
|---|---|---|---|
| 4,016,043 | A | 4/1977 | Schuurs et al. |
| 4,018,653 | A | 4/1977 | Mennen |
| 4,424,279 | A | 1/1984 | Bohn et al. |
| 6,719,973 | B1 | 4/2004 | Ding et al. |
| 8,771,967 | B2 * | 7/2014 | Banaei ............... G01N 33/564 435/7.1 |
| 2012/0129197 | A1 | 5/2012 | Banaei | |

FOREIGN PATENT DOCUMENTS

WO   WO01/79829 A1   10/2001

OTHER PUBLICATIONS

Gosh et al, Cellular Immunology, 2006; vol. 243, pp. 48-57.*
Duvigneau et al, Journal of Immunological Methods, 2007, vol. 324, pp. 38-47.*
Smits et al, Oncologist; 2008; vol. 13, 859-875.*
Wapenaar et al, Journal of Autoimmunity, 2004, vol. 23, pp. 183-190.*
Skinnider et al, Blood, 2001, vol. 97, pp. 250-255.*
Bigos et al., "Nine Color Eleven Parameter Immunophenotyping Using Three Laser Flow Cytometry," *Cytometry* 36:36-45, 1999.
Daneshvar et al. "Detection of biomolecules in the near-infrared spectral region via a fiber optic immunosensor," *Journal of Immunological Methods* 226:119-128, 1999.
Durig et al., "Fourier Transform Raman Spectroscopy of Brightly Colored Commercially Available Dyestuffs and Pigments," *Journal of Raman Spectroscopy* 24:281-285, 1993.
Eriksson et al. "Lipid and water diffusion in bicontinuous cubic phases measured by NMR," *Biophysical Journal* 64:129-136, Jan. 1993.
Fooladi et al., "Study of T-cell stimulation and cytokine release induced by *Staphylococcal enterotoxin* type B and monophosphoryl lipid A," *Arch Med Sci* 5(3):335-341, 2009.
Fu et al., "A microfabricated fluorescence-activated cell sorter," *Nature Biotechnology* 17:1109-1111, Nov. 1999.
Hemmi et al., "Small anti-viral compounds activate immune cells via the TLR7 MyD88-dependent signaling pathway," *Nature Immunology* 3(2):196-200, 2002.
Lakowicz et al., "Time-Resolved Fluorescence Spectroscopy and Imaging of DNA Labeled with DAPI and Hoechst 33342 Using Three-Photon Excitation," *Biophysical Journal* 72:567-578, Feb. 1997.
Lewis et al., Erratum to "The use of Fourier Transform Infrared (FT-IR) spectroscopy to study the state of heterobifunctional reactive dyes," *Dyes and Pigments* 42: 197, 1999.
Nowroozalizadeh et al., "Studies on toll-like receptor stimuli responsiveness in HIV-1 and HIV-2 infections," *Cytokine* 46:325-331, 2009.
Peet et al., "Synthesis and Antiallergic Activity of Some Quinolinones and Imidazoquinolinones," *J. Med. Chem.* 28:298-302, 1985.
Petkovic-Duran et al., "Short Technical Reports: Chaotic micromixing in open wells using audio-frequency acoustic microstreaming," *Biotechniques* 47:827-834, 2009.
Rahman et al., "Infrared and Raman Spectra of a Single Resin Bead for Analysis of Solid-Phase Reactions and Use in Encoding Combinatorial Libraries," *The Journal of Organic Chemistry* 63:6196-6199, 1998.
Rapaport et al., "Visible light emission from dyes excited by simultaneous absorption of two different frequency beams of light," *Applied Physics Letters* 74(3):329-331, Jan. 18, 1999.
Tawa et al., "Polarized Light-Induced Anisotropy in Polymer Films Doped with Az Dyes in the Photostationary State Studied by IR Spectroscopy," *Materials Research Society Symposium Proceedings* 488:885-890, 1998.
Youvan et al., "Calibration of Fluorescence Resonance Energy Transfer in Microscopy Using Genetically Engineered GFP Derivatives on Nickel Chelating Beads," *Biotechnology* 3:1-18, 1997.

* cited by examiner

*Primary Examiner* — Bridget E Bunner
*Assistant Examiner* — Fozia Hamud
(74) *Attorney, Agent, or Firm* — Seed IP Law Group LLP

(57) ABSTRACT

This disclosure relates generally to the field of immunological-based diagnostic assays including an assay to measure cell-mediated immunoresponsiveness. The present disclosure teaches determination of the state, progression and/or severity of disease conditions based on a subject's cell-mediated immunoresponsiveness. The assay contemplated herein is capable of integration into standard pathology architecture to provide a diagnostic reporting system and to facilitate point of care clinical management.

14 Claims, 4 Drawing Sheets

TLR AGONIST-ENHANCED IN VITRO ASSAY OF CELL MEDIATED IMMUNE RESPONSIVENESS

FILING DATA

This application is associated with and claims priority from U.S. Provisional Patent Application No. 61/480,913, filed on 29 Apr. 2011, entitled "An assay of cell mediated immune responsiveness", the entire contents of which, are incorporated herein by reference.

FIELD

This disclosure relates generally to the field of immunological-based diagnostic assays including an assay to measure cell-mediated immunoresponsiveness. The present disclosure teaches determination of the state, progression and/or severity of disease conditions based on a subject's cell-mediated immunoresponsiveness. The assay contemplated herein is capable of integration into standard pathology architecture to provide a diagnostic reporting system and to facilitate point of care clinical management.

BACKGROUND

Bibliographic details of the publications referred to by author in this specification are collected alphabetically at the end of the description.

Reference to any prior art in this specification is not, and should not be taken as an acknowledgment or any form of suggestion that this prior art forms part of the common general knowledge in any country.

Immunological-based diagnostic assays are important tools in detecting a variety of disease conditions. The effectiveness of these types of assays lies in part in the specificity of components within the immune system. Notwithstanding this specificity, immunological-based diagnostics are not necessarily always sensitive enough to detect low levels of innate and/or adaptive immune response activity, such as in response to a low grade infection or in the presence of a persistent low level infection or in subjects with active or latent disease states. There is a need to develop diagnostic assays with enhanced sensitivity in relation to cell-mediated immunoresponsiveness.

One form of immunological-based diagnostic assay involves the stimulation of T-cells with antigens or mitogens in either isolated cell culture or in whole blood culture followed by the detection of effector molecules such as cytokines produced by the stimulated T-cells (also referred to as effector T-cells). The effector molecules are generally detected using techniques such as enzyme immunoassays, multiplex head analysis, ELISpot and flow cytometry. Such assays are useful for detecting disease-specific T-cell responses. An example of a T-cell assay is QuantiFERON (Registered Trade Mark: Cellestis Limited). This is hereinafter referred to as "QFT" and is a test based on an Interferon-γ (IFN-γ) release assay (IGRA). Another assay employs the direct stimulation of highly purified human T-cells using anti-CD3 antibodies (a T-cell receptor agonist) and the Toll-like receptor (TLR) agonist, R848. However, not all effector molecules were detected and the assay is not suitable for whole blood.

The ability to quickly assess cell-mediated immunity and with a high degree of sensitivity is of clinical importance. A clinician needs to have an appreciation of the development of a disease state and its effect on the host's immune system. There is a need, however, to improve the sensitivity of assays of cell-mediated immunoresponsiveness in a subject.

SUMMARY

Enabled herein is a method for detecting a cell-mediated immune response in a subject, the method comprising incubating lymphocytes from the subject with:
 (i) an antigen; and
 (ii) a limiting amount of a Toll-like receptor (TLR) agonist; and then screening for levels of effector molecules produced by activated lymphocytes.

By "limiting amount" of the TLR agonist means an amount of agent which:
 (i) induces minimal background response when the agent is incubated with lymphocytes in the absence of an antigen; and/or
 (ii) is present in a ratio of agent to antigen of from 1:500 to 1:1.5; and/or
 (iii) has a concentration less than the amount of antigen; and/or
 (iv) is a sub-optimal amount of agent which would otherwise be required to generate a response in a QFT-Nil antigen tube.

The co-incubation of antigen and the limiting amount of TLR agonist with lymphocytes results in a more sensitive assay, enabling earlier detection of lymphocyte stimulation than would otherwise be possible. The increased sensitivity includes at least a 10% increased detection of effector molecules compared to co-incubation with non-limiting amounts of the TLR agonist. The ability to increase the sensitivity of a cell-mediated immune response assay may also enable less sensitive means of detection of effector molecules. Furthermore, the magnitude of the cell-mediated immune response detected in the assay presently disclosed can be correlated to the disease state, progression and/or severity. Hence, the present disclosure teaches an assay of cell-mediated immunoresponsiveness in a subject.

A method for measuring cell-mediated immune response activity in a subject is therefore provided herein, the method comprising contacting lymphocytes from the subject with an antigen and a limiting amount of a TLR agonist and measuring the presence or elevation in the level of an immune effector molecule from immune cells wherein the presence or level of the immune effector molecule is indicative of the level of cell-mediated responsiveness of the subject.

TLR agonists include TLR-7/8, TLR-4, TLR-3 or TLR-2 agonist. Examples include the imidazoquinoline, R848, lipomannan and poly (I:C). In an embodiment, the TLR agonist is R848 which is a TLR 7/8 agonist.

Usefully, the subject is a human and the sample is undiluted whole blood. Alternatively, the sample is whole blood which comprises from about 10% to 100% by volume of the sample to be assayed or comprises from about 50% to 100% by volume of the sample to be assayed or comprises from about 80% to 100% by volume of the sample to be assayed. The sample volume may be in microliter or milliliter amounts such as from 0.5 µl to 5 ml. Conveniently, the whole blood is collected in a tube comprising heparin and the immune effector molecule is IFN-γ. Generally, the immune effectors are detected with antibodies specific for same such as using ELISA or an ELISpot.

The subject may have an infection by a pathogenic agent selected from *Mycobacterium* species such as *Mycobacterium tuberculosis* or tuberculosis (TB), *Staphylococcus* species, *Streptococcus species, Borrelia* species, *Escherichia coli. Salmonella* species, *Clostridium* species, *Shigella* species, *Proteus* species, *Bacillus* species, Herpes virus, Hepatitis B or C virus and Human immune deficiency virus (HIV) or a disease resulting therefrom.

The subject may alternatively have a disease condition selected from Celiac's disease, autoimmune diabetes, alopecia areata, ankylosing spondylitis, antiphospholipid syndrome, autoimmune Addison's disease multiple sclerosis, autoimmune disease of the adrenal gland, autoimmune hemolytic anemia, autoimmune hepatitis, autoimmune oophoritis and orchitis, Behcet's disease, bullous pemphigoid cardiomyopathy, celiac Sprue-dermatitis, chronic fatigue syndrome (CFIDS), chronic inflammatory demyelinating, chronic inflammatory polyneuropathy, Churg-Strauss syndrome, cicatricial pemphigoid, crest syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), lichen planus, lupus, Meniere's disease, mixed connective tissue disease, multiple sclerosis, myasthenia gravis, myocarditis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, systemic lupus erythematosus, Takayasu arteritis, temporal arteritis/giant cell arteritis, ulcerative colitis, uveitis, vasculitis, vitiligo and inflammatory bowel disease.

The subject may alternatively have a cancer selected from ABL1 protooncogene. AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, hone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extrahepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor.

The subject may alternatively be exposed to a toxicant.

In the above aspects, the antigen may be derived from the pathogenic agent, be associated with the disease condition or cancer or be the toxicant. Alternatively, the infection, disease condition, cancer or toxicant may suppress cell-mediated immunity in which case any antigen to which the subject has been prior exposed could be employed.

Another aspect taught herein is the use of a limiting amount of a TLR agonist in the manufacture of a diagnostic assay of cell-mediated immune responsiveness by the method of incubating lymphocytes from the subject with a limiting amount of the agonist and detecting the presence or elevation in effector molecules.

A method is also provided of allowing a user to determine the status of cell-mediated immunoresponsiveness of a subject, the method including:

(a) receiving data in the form of levels or concentrations of an immune effector molecule which, relative to a control, provide a correlation as to the state of cell-mediated immunoresponsiveness in a subject, via a communications network, the immune effector molecule measured after exposure of lymphocytes to an antigen and a limiting amount of a TLR agonist;

(b) processing the data via univariate or multivariate analysis to provide an immunoresponsiveness value;

(c) determining the status of the subject in accordance with the results of the immunoresponsiveness value in comparison with predetermined values; and (d) transferring an indication of the status of the subject to the user via the communications network.

DETAILED DESCRIPTION

Figure 1:
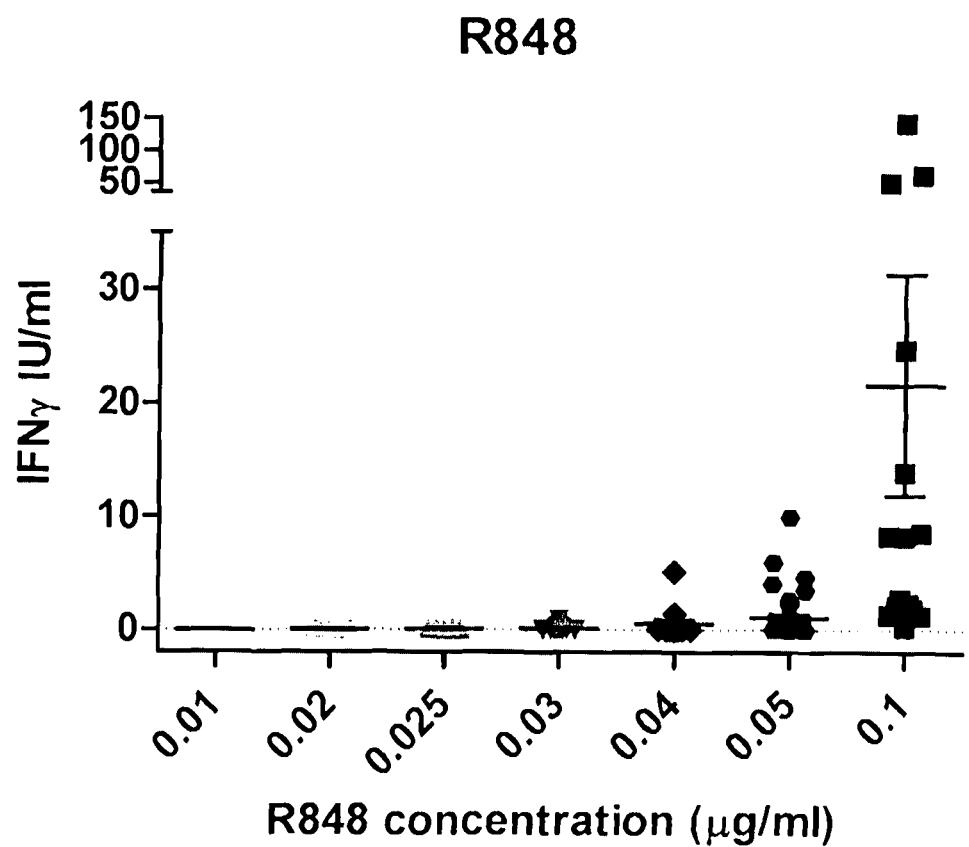
FIG. 1 is a graphical representation showing IFN-γ responses from whole blood cultures exposed to different concentrations of the TLR agonist, R848 (0.01 µg/ml to 0.1 µg/ml). The experiment was conducted in tubes without antigen (Nil antigen) comprising R848 and the blood sample. The tubes are QFT-Nil antigen tubes.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method step or group of elements or integers or method steps.

As used in the subject specification, the singular forms "a", "an" and "the" include plural aspects unless the context clearly dictates otherwise. Thus, for example, reference to "a T-cell" includes a single T-cell, as well as two or more T-cells; reference to "an agent" includes a single agent, as well as two or more agents; reference to "the disclosure" includes single or multiple aspects taught by the present disclosure; and so forth. Aspects described are encompassed by the term "invention". All aspects are enabled within the width of the claims. The terms "T-cells" and "T-lymphocytes" are used interchangeably herein. An "immune cell" includes a lymphocyte such as NK cells.

Reference to an "agent", "reagent", "molecule" and "compound" includes single entities and combinations of two or more of such entities. A "combination" also includes multi-part such as a two-part composition where the agents are provided separately and used or dispensed separately or admixed together prior to dispensation. For example, a multi-part assay pack may have an antigen against which a cell-mediated immune response is to be measured and TLR agonist. Hence, this aspect of the present disclosure includes agents dried and loose or immobilized to a compartment wall or solid support in an assay pack.

Enabled herein is a method for detecting a cell-mediated immune response in a subject, the method comprising incubating lymphocytes from the subject with:

(i) an antigen; and
(ii) a limiting amount of a TLR agonist;

and then screening for levels of effector molecules produced by activated lymphocytes.

Lymphocytes are activated by co-incubation with antigen. The limiting amounts of TLR agonist enhances the early detection of effector molecules.

The term "TLR agonist" is an example of an agent which potentiates the innate immune system. Other suitable terms include potentiators, stimulants, activators and inducers of the innate immune system.

An innate immunity stimulant includes a TLR agonist. TLR agonists include an imidazoquinoline compound such as R848 (TLR-7/8 ligand), Pam3CSK4 (TLR-2 ligand). Lipomannan (TLR-2 ligand), poly(I:C)-[TLR-3 ligand], Lipopolysaccharide (TLR-4 ligand), and CpG oligodeoxynucleotides (TLR-9 ligand). In terms of selecting a TLR agonist, in decreasing order, agonists are selected from agonists for TLR-7/8>TLR-4>TLR-3>TLR-2.

R848 is disclosed by Nowroozalizadeh et al. (2009) *Cytokine* 46:325-31. Hemmi et al. (2002) *Nature Immunology* 3:196-200 and Peel et al. (1985) *J Med Chem* 28:298-302. Reference to "imidazoquinoline" or "R848" includes an imidazoquinoline derivative.

The present disclosure teaches augmentation of production of effector molecules from lymphocytes exposed to an antigen. Such lymphocytes are "activated" or "stimulated" lymphocytes. The augmentation occurs by exposing the cells to a limiting amount of a TLR agonist. The level of the response is greater in the presence of the antigen and limiting amounts of TLR agonist than the sum of the separate responses in the presence of antigen or limiting amount of TLR agonist alone or when the TLR agonist is not limiting. This enables a more sensitive assay in order to assess the cell-mediated immune responsiveness of a subject. The present disclosure, therefore, enables an assay to detect, assess or otherwise monitor a cell-mediated response in a subject by measuring the presence or level of effector molecules from T-cells stimulated by an antigen in the presence of a TLR agonist but in limiting amounts. The assay also enables earlier detection of cell-mediated responsiveness. In an embodiment, the assay taught therein enhances the sensitivity of a cell-mediated assay which may enable less sensitive detection assays to be employed. Furthermore, the extent or magnitude of the cell-mediated immune response is proposed to be reflective or informative of the state, progression and/or severity of a disease condition. For example, the magnitude of the response may determine if a subject has a latent or active or acute infection or disease condition.

An additional agent may also be added to modulate the activity of regulatory T-cells (T-reg cells). The latter encompasses inhibiting the suppressor function of T-reg cells. Agents which modulate T-reg cells encompassed herein include a CD25 ligand; sense or antisense oligonucleotide to genetic material encoding JAK1 or TYK2: a neutralizing antibody; a CpG containing oligonucleotide; an oligonucleotide acting as a TLR modulating agent; and other TLR modulating agents.

In a particular embodiment, the T-reg cells are immune response suppressor cells the activity of which is inhibited.

A "CpG molecule" means an oligonucleotide comprising a CpG sequence or motif.

By "limiting amount" in respect of the TLR agonist includes an amount agent which, on its own, induces no or minimal background response using QFT-Nil antigen tubes; a ratio of agent to antigen of 1:1.5 to 1:500 including 1:1.5, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:101, 1:102, 1:103, 1:104, 1:105, 1:106, 1:107, 1:110, 1:111, 1:112, 1:113, 1:114, 1:115, 1:116, 1:117, 1:118, 1:119, 1:120, 1:121, 1:122, 1:123, 1:124, 1:125, 1:126, 1:127, 1:128, 1:129, 1:130, 1:131, 1:132, 1:133, 1:134, 1:135, 1:136, 1:137, 1:138, 1:139, 1:140, 1:141, 1:142, 1:143, 1:144, 1:145, 1:146, 1:147, 1:148, 1:149, 1:150, 1:151, 1:152, 1:153, 1:154, 1:155, 1:156, 1:157, 1:158, 1:159, 1:159, 1:160, 1:161; 1:162, 1:163, 1:164, 1:165, 1:166, 1:167, 1:168, 1:169, 1:170, 1:171, 1:172, 1:173, 1:174, 1:175, 1:176, 1:177, 1:178, 1:179, 1:180, 1:181, 1:182, 1:183, 1:184, 1:185, 1:186, 1:187, 1:188, 1:189, 1:190, 1:191, 1:192, 1:193, 1:194, 1:195, 1:196, 1:197, 1:198, 1:199, 1:200, 1:250, 1:300, 1:350, 1:400, 1:450 or 1:500 or an amount in between; an amount of agent which is less than the antigen; and/or a sub-optimal amount of agent which would otherwise be required to generate a response in the QFT-Nil antigen tube. The assay herein produces an at least 10% improvement in sensitivity in terms of detection of effector molecules. By "at least 10%" includes from about 10% to about 50%.

Amounts of the TLR agonist used in the assay will vary depending on the agonist and the assay conditions and concentrations of antigen and other components. In relation to R848, a limiting amount of this TLR agonist includes from 0.01 µg/ml to about 10 µg/ml of assay fluid. This encompasses 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 and 10 µg/ml. In an embodiment, from about 0.05 µg/ml to about 1.0 µg/ml R848 is used.

The present disclosure provides a means to determine the responsiveness of cell-mediated immunity in a subject and, in turn, teaches the determination of whether a disease condition or an agent induces or is associated with immunosuppression. The method also enables diagnosis of infectious diseases, pathological conditions, determination of the level of immunocompetence and assessing of immune cell responsiveness to endogenous or exogenous agents as well as assessing exposure to a toxic agent such as beryllium or other toxicants. The assay also enables screening of subjects previously exposed to a particular antigen, such as an antigen associated with a disease, infection or contaminant.

Accordingly, an aspect taught herein contemplates a method for measuring cell-mediated immune response activity in a subject, the method comprising contacting lymphocytes from the subject with an antigen and a limiting amount of a TLR agonist and measuring the level of an immune effector molecule produced by immune cells wherein the level of the immune effector molecule is indicative of the level of cell-mediated immunoresponsiveness of the subject.

Another aspect contemplated herein is a method for measuring cell-mediated immune response activity in a subject, the method comprising contacting lymphocytes from the subject with an antigen and a limiting amount of a TLR agonist and measuring the elevation in the level of an immune effector molecule from immune cells wherein the level of the immune effector molecule is indicative of the level of cell-mediated responsiveness of the subject wherein the level of responsiveness is indicative of the presence or absence or level or stage of a disease or condition selected from the list comprising an infection by a pathogenic agent, an autoimmune disease, a cancer, an inflammatory condition and exposure to a toxic agent.

Yet another aspect enabled herein is a method for measuring cell-mediated immune response activity in a subject, the method comprising contacting lymphocytes from the subject with an antigen and a limiting amount of a TLR agonist and measuring the elevation in the level of an immune effector molecule from immune cells wherein the level of the immune effector molecule is indicative of the level of cell-mediated responsiveness and is indicative of the presence or absence or level or stage of a disease or condition selected from the list comprising an infection by a pathogenic agent, an autoimmune disease, a cancer, an inflammatory condition and exposure to a toxic agent.

Still another aspect taught by the present disclosure is an assay to detect the presence, absence, level or stage of a disease or condition in a subject, the method comprising contacting lymphocytes from the subject with an antigen and a limiting amount of a TLR agonist and measuring the elevation in the level of an immune effector molecule from immune cells wherein the level of the immune effector molecule is indicative of the disease or condition.

The present disclosure further contemplates a method for determining whether an agent induces immunosuppression in a subject, the method comprising contacting lymphocytes from the subject after exposure to the agent with an antigen and a limiting amount of a TLR agonist and measuring the presence and level of an effector molecule from the lymphocytes wherein the level of the effector molecule determines the level of immunosuppression induced by the agent.

In accordance with this aspect, the agent may be a medicament or an environmental toxicant.

In an embodiment, the lymphocytes are comprised within a blood sample. In an embodiment, the blood sample is co-stimulated with an antigen and a limiting amount of R848 or other imidazoquinoline.

Hence, the present disclosure teaches a method for measuring cell-mediated immune response activity in a subject, the method comprising contacting lymphocytes from the subject with an antigen and a limiting amount of R848 or its functional equivalent and measuring the level of an immune effector molecule produced by immune cells wherein the level of the immune effector molecule is indicative of the level of cell-mediated immunoresponsiveness of the subject.

Another aspect taught by the present disclosure contemplates a method for measuring cell-mediated immune response activity in a subject, the method comprising contacting lymphocytes from the subject with an antigen and a limiting amount of R848 or its functional equivalent and measuring the elevation in the level of an immune effector molecule from immune cells wherein the level of the immune effector molecule is indicative of the level of cell-mediated responsiveness of the subject wherein the level of responsiveness is indicative of the presence or absence or level or stage of a disease or condition selected from the list comprising an infection by a pathogenic agent, an autoimmune disease, a cancer, an inflammatory condition and exposure to a toxic agent.

A use is also provided for a limiting amount of a TLR agonist in the manufacture of a diagnostic assay of cell-mediated immune responsiveness by the method of incubating lymphocytes with a limiting amount of the agonist and detecting the presence or elevation in an effector molecule.

In another embodiment, taught herein is a method for detecting whether a disease condition is inducing immunosuppression in a subject the method comprising contacting lymphocytes from the subject with a disease condition with an antigen and a limiting amount of a TLR agonist measuring the presence or level of an immune effector molecule from the lymphocytes wherein the level of the immune effector molecule is indicative of the extent of immunosuppression induced or associated with the disease condition.

A use is also provided for an antigen and a limiting amount of a TLR agonist in the manufacture of a diagnostic assay of cell-mediated immune responsiveness by the method of incubating lymphocytes with the agonist and detecting the presence or elevation in an effector molecule.

This use includes the use for detecting or monitoring the presence, absence, level or stage of a disease or condition such as an infection by a pathogenic agent, an autoimmune disease, a cancer, an inflammatory condition and/or exposure to a medicament or a toxic agent such as a beryllium or other environmental toxicant. Measuring "an immune effector molecule" includes measuring one or more different types of molecules.

The present disclosure further enables a method for measuring cell-mediated immune response activity in a subject, the method comprising contacting a regulatory T-cell from the subject with an agent selected from (i) an inhibitor of suppressor regulatory T-cells; and (ii) an activator of immune augmenting cells or a subset thereof; and further contacting T-cells with an antigen and a limiting amount of a TLR agonist and measuring the elevation in the level of an immune effector molecule from immune cells wherein the level of the immune effector molecule is indicative of the level of cell-mediated responsiveness of the subject.

Examples of inhibitors or modulators of T-reg function include CD25 ligands such as but not limited to a polyclonal or monoclonal antibody to CD25 or an antigen-binding fragment thereof, humanized or deimmunized polyclonal or monoclonal antibodies to CD25 or a recombinant or synthetic form of the polyclonal or monoclonal antibodies. Other examples of agents include sense or antisense nucleic and molecules directed to the mRNA or DNA (i.e. genetic material) encoding Janus Tyrosine Kinase 1 (JAK1) or Tyrosine Kinase 2 (TYK2) or small molecule inhibitors of JAK1 or TYK2 proteins. Reference to "small molecules" includes immunoglobulin new antigen receptors (IgNARs) as described in International Patent Publication No. WO 2005/118629. Yet still further examples of suitable agents stimulating agents such as CpG molecules which act via Toll-like receptors (TLRs) and/or other mechanisms. Hence, CpG containing oligonucleotides and an oligonucleotide acting as a TLR modulating agent also form part of the present disclosure.

A single type of agent may be used or two or more types of agents may be employed to modulate T-reg cells. For example, the assay may be conducted with a CD25 ligand and a JAK1/TYK2 sense or antisense oligonucleotide; a CD25 ligand and a TLR modulating agent; a JAK1/TYK2 sense or antisense oligonucleotide and a TLR modulating agent; or a CD25 ligand, a JAK1/TYK2 sense or antisense oligonucleotide and a TLR modulating agent. Alternatively, just one type of agent is employed. In another alternative, a CpG comprising oligonucleotide and a TLR modulating agent is used.

Reference to a "subject" includes a human or non-human species including primates, livestock animals (e.g. sheep, cows, pigs, horses, donkey, goats), laboratory test animals (e.g. mice, rats, rabbits, guinea pigs, hamsters), companion animals (e.g. dogs, cats), avian species (e.g. poultry birds, aviary birds), reptiles and amphibians. The present subject matter has applicability in human medicine as well as having livestock and veterinary and wild-life applications which includes the horse, dog and camel racing industries. For example, the assay of the present disclosure may be routinely carried out on horses before and/or after heavy exertion (such as a race) to screen for evidence of exercise-induced pulmonary hemorrhage (EIPH). All horses exhibit some form of EIPH to some degree during exercise. However, sub-clinical forms of EIPH can be hard to detect.

Reference to a "human" includes particular populations of humans such as pediatric, elderly and infirmed populations of humans as well as particular cohorts or populations of humans of a particular ethnicity.

In another embodiment, the subject is a human and the cell-mediated immune response assay is used in screening for responsiveness to pathogenic microorganisms, viruses and parasites, potential for development or monitoring autoimmune conditions. Celiac's disease, monitoring a subject's response to oncological challenge and for determining the presence of any immunodeficiency or immunosuppression. The latter may occur, for example, due to certain medicaments including various chemotherapeutic agents. Alternatively, exposure to environmental toxicants and pollutants.

The immune effector molecules may be any of a range of molecules which are produced in response to cell activation or stimulation by an antigen. Although an interferon (IFN) such as IFN-$\gamma$ is a particularly useful immune effector molecule, others include a range of cytokines such as interleukins (IL), e.g. IL-2, IL-4, IL-6, IL-6 (CXCL8), IL-10, IL-12, IL-13, IL-16 (LCF) or IL-17, IL-1$\alpha$ (IL-1F1), IL-1$\beta$ (IL-1F2), IL-1r$\alpha$ (IL-1F3). Tumor Necrosis Factor alpha (TNF-$\alpha$), Transforming Growth Factor beta (TGF-$\beta$), a Colony Stimulating Factor (CSF) such as Granulocyte (G)-CSF or Granulocyte Macrophage (GM)-CSF, complement component 5a (C5a), Gro$\alpha$ (CXCL1), sICAM-1 (CD54), IP-10 (CXCL10), I-TAC (CXCL11), MCP-1 (CCL2), MIF (GIF). MIP-1$\alpha$ (CCL3), MIP-1$\beta$ (CCL4), RANTES (CCL5) or MIG (CXCL9).

The present disclosure also enables a method for measuring cell-mediated immune response activity in a subject, the method comprising contacting lymphocytes from the subject with an antigen and a limiting amount of a TLR agonist and measuring the level of an immune effector molecule from immune cells wherein the level of the immune effector molecule is indicative of the level of cell-mediated responsiveness of the subject.

The assay taught herein enables detection of the presence or absence or level or stage of a disease or condition in a subject such as infection by a pathogenic agent, an autoimmune disease, cancer, exposure to an inflammatory agent exposure to a medicament, exposure to a toxic agent such as beryllium or other toxicant or pollutant and immunodeficiency or immunosuppression such as induced by a disease condition.

The TLR agonist may be free standing in a reactive vessel or may be immobilized to a solid support such as a bead or a side or bottom of a reaction vessel. The agonist may also be in dried form which is re-constituted prior to or during use. Similarly, the antigen may be free standing or immobilized in a reactive vessel such as to the vessel itself or a bead or other solid support.

In an embodiment, the sample collected from the subject is generally deposited into a blood collection tube. A blood collection tube includes a blood draw tube or other similar vessel. Conveniently, when the sample is whole blood, the blood collection tube is heparinized. Alternatively, heparin is added to the tube after the blood is collected. Notwithstanding that whole blood is particularly contemplated and a most convenient sample, the present disclosure extends to other samples containing immune cells such as lymph fluid, cerebral fluid, tissue fluid and respiratory fluid including nasal and pulmonary fluid as well as samples having undergone cell depletion. Reference to "whole blood" includes whole blood which has not been diluted such as with tissue culture, medium, reagents, excipients, etc. In one embodiment, the term "whole blood" includes an assay sample (i.e. reaction mixture) comprising at least 10% by volume whole blood. The term "at least 10% by volume" includes blood volumes of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by volume of total assay volume of the reaction mixture. Additional agents may be added such as culture media, enzymes, excipients antigen and the like without departing from the sample comprising "whole blood".

Blood volumes may be from about 0.5 µl to 200 ml. Examples include 0.5 µl, 1.5 µl, 10 µl, 20 µl, 50 µl, 100 µl, 500 µl, 1 ml, 5 ml, 10 ml, and 20 ml. The present disclosure also enables the use of acoustic microstreaming to improve the mixing of components in the assay. Acoustic microstreaming is disclosed in International Patent Application No. PCT/AU01/00420 and in Petkovic-Duran et al. (2009) *Biotechniques* 47:827-834.

Hence, contemplated herein is a method of mixing one or more lymphocytes and an antigen and a limiting amount of a TLR agonist in a vessel, the method comprising providing from about 0.5 µl to 150 µl of fluid comprising the components in the vessel so as to establish a discontinuity in acoustic impedance and applying an acoustic signal to cause mixing within the fluid. A second acoustic signal may also be applied, the first and second signals having respective frequencies each selected from about 1 Hz to about 20,000 Hz in an alternating manner to effect chaotic mixing within the fluid.

The use of blood collection tubes is compatible with standard automated laboratory systems and these are amenable to analysis in large-scale and random access sampling. Blood collection tubes also minimize handling costs and reduce laboratory exposure to whole blood and plasma and, hence, reduce the risk of laboratory personnel from contracting a pathogenic agent such as HIV or Hepatitis B virus (HBV) or Hepatitis C virus (HCV).

Combining the incubation step with the collection tube is particularly efficacious and enhances the sensitivity of the assay as does the optional feature of incubating the cells in the presence of a simple sugar such as dextrose or glucose.

The cells of the cell-mediated immune system lose the capacity to mount an immune response in whole blood after extended periods following blood draw from the subject, and responses without intervention are often severely reduced or absent 24 hours following blood draw. The reduction of labor and need for specialized plasticware allows cell-mediated immune stimulation with antigens to be performed at the point of care locations such as physicians' offices, clinics, outpatient facilities and veterinary clinics or on farms. Once antigen stimulation is complete, the requirement for fresh and active cells no longer exists. IFN-γ and other cytokines or immune effector molecules are stable in plasma and, thus, the sample can be stored, or shipped without special conditions or rapid time requirements.

the incubation step may be from 1 to 50 hours, such as 1 to 40 hours or 8 to 24 hours or a time period in between including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 hours. A period of 24 hours is particularly convenient.

The ability to measure cell-mediated immunity is important for assessing a subject's ability to respond to an infection by a pathogenic agent such as a microorganism or virus or parasite, to mount an autoimmune response such as in autoimmune diabetes or to protect against cancers or other oncological conditions or to detect an inflammatory condition or to detect exposure or sensitivity of a subject to a toxic agent such as beryllium. The assay described herein also enables detection of disease conditions which lead to immunosuppression or immunosuppresion induced by medicaments Consequently, reference to "measuring a cell-mediated immune response in a subject" includes and encompasses immune diagnosis of infectious and autoimmune diseases, a marker for immunocompetence as well as a marker for inflammatory diseases, cancer and toxic agents. Importantly, the combined innate and/or adaptive immune responsiveness is determined. Furthermore, the ability to use small blood volumes enables assays to be readily conducted on, for example, the pediatric, elderly and infirmed populations. The assay herein enables early detection or more sensitive detection of immunoresponsiveness.

In an embodiment, disease conditions leading to immunosuppression include chronic infection and cancer. Medicaments which can lead to immunosuppression include those used to treat rheumatoid arthritis, cancer and inflammatory bowel disease.

Pathogenic or infectious agents include bacteria, parasites and viruses. Examples of bacteria include Gram positive and Gram negative microorganisms such as *Mycobacterium* species, *Staphylococcus* species, *Streptococcus* species, *Escherichia coli, Salmonella* species, *Clostridium* species, *Shigella* species, *Proteus* species, *Bacillus* species. *Hemophilus* species, *Borrelia* species amongst others. *Mycobacterium tuberculosis* is a particularly useful target as well as conditions arising from infection by *M. tuberculosis* such as tuberculosis (TB). Examples of viruses include Hepatitis virus (Hepatitis B virus and Hepatitis C virus), Herpes virus and Human immune deficiency virus (HIV) as well as diseases resulting therefrom. Parasites include *Plasmodium* species, ringworm, liver parasites and the like. Other pathogenic agents include eukaryotic cells such as yeasts and fungi.

Autoimmune diseases contemplated herein for detection include inter alia alopecia areata, ankylosing spondylitis, antiphospholipid syndrome, autoimmune Addison's disease multiple sclerosis, autoimmune disease of the adrenal gland, autoimmune hemolytic anemia, autoimmune hepatitis, autoimmune oophoritis and orchitis, Behcet's disease, bullous pemphigoid, cardiomyopathy, celiac sprue-dermatitis, chronic fatigue syndrome (CFIDS), chronic inflammatory demyelinating, chronic inflammatory polyneuropathy. Churg-Strauss syndrome, cicatricial pemphigoid, crest syndrome, cold agglutinin disease. Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), lichen planus, lupus, Meniere's disease, mixed connective tissue disease, multiple sclerosis, myasthenia gravis, myocarditis, pemphigus vulgaris, pernicious anemia, polyancritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, systemic lupus erythematosus, Takayasu arteritis, temporal arteritis/giant cell arteritis, ulcerative colitis, uveitis, vasculitis and vitiligo.

It is generally important to assess the potential or actual cell-mediated responsiveness in subjects exposed to these infectious entities. The method of the present disclosure can also be used to detect the presence or absence of these conditions as well as the level or stage of disease process.

Other disease conditions which can lead to immunosuppression include inflammatory disease conditions.

Examples of inflammatory disease conditions contemplated by the present disclosure include but are not limited to those disease and disorders which result in a response of redness, swelling, pain, and a feeling of heat in certain areas that is meant to protect tissues affected by injury or disease. Inflammatory diseases which can be treated using the methods of the present disclosure include, without being limited to, acne, angina, arthritis, aspiration pneumonia, disease, empyema, gastroenteritis, inflammation, intestinal flu, NEC, necrotizing enterocolitis, pelvic inflammatory disease, pharyngitis, PID, pleurisy, raw throat, redness, rubor, sore throat, stomach flu and urinary tract infections, chronic inflammatory demyelinating polyneuropathy, chronic inflammatory demyelinating polyradiculoneuropathy, chronic inflammatory demyelinating polyneuropathy, chronic inflammatory demyelinating polyradiculoneuropathy. In terms of non-human applications, the present disclosure extends to detecting EIPH in horses and various conditions in animals such as facial tumor disease in the Tasmanian Devil.

Cancer therapy also is somewhat dependent on cell-mediated immunity and the cancer itself or drugs used to treat cancer can lead to immunosuppression. Cancers contemplated herein include: a group of diseases and disorders that are characterized by uncontrolled cellular growth (e.g. formation of tumor) without any differentiation of those cells into specialized and different cells. Such diseases and disorders include ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia. Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor.

In the above aspects, the antigen may be derived from the pathogenic agent, be associated with the disease condition or cancer or be the toxicant. Alternatively, the infection, disease condition, cancer or toxicant may suppress cell-mediated immunity in which case any antigen to which the subject has been prior exposed could be employed.

Another aspect taught herein is the use of a limiting amount of a TLR agonist in the manufacture of a diagnostic assay of cell-mediated immune responsiveness by the method of incubating lymphocytes from the subject with a limiting amount of the agonist and detecting the presence or elevation in effector molecules.

The detection of the immune effector molecules may be measured at the protein or nucleic acid levels. Consequently, reference to "presence or level" of the immune effector molecule includes direct and indirect data. For example, high levels of cytokine mRNA are indirect data showing increased levels of the cytokine.

Ligands to the immune effectors are particularly useful in detecting and/or quantitating these molecules. Antibodies to the immune effectors are particularly useful. Techniques for the assays contemplated herein are known in the art and include, for example, radioimmunoassay, sandwich assays, ELISA and ELISpot. Reference to "antibodies" includes parts of antibodies, mammalianized (e.g. humanized) antibodies, deimmunized antibodies, recombinant or synthetic antibodies and hybrid and single chain antibodies. For skin tests, in humans, humanized or deimmunized antibodies are particularly contemplated herein to detect effector molecules.

Both polyclonal and monoclonal antibodies are obtainable by immunization with the immune effector molecules or antigenic fragments thereof and either type is utilizable for immunoassays. Methods of obtaining both types of sera are well known in the art: Polyclonal sera are less preferred but are relatively easily prepared by injection of a suitable laboratory animal with an effective amount of the immune effector, or antigenic part thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly useful because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect enabled herein, therefore, is a method for detecting an immune effector molecule in a sample comprising lymphocytes from a subject, the method comprising contacting the sample or an aliquot of the sample with an antibody specific for the immune effector molecule or an antigenic fragment thereof for a time and under conditions sufficient for an antibody-effector complex to form, and then detecting the complex wherein the immune effector molecule is generated after incubation of the lymphocytes with one an antigen and a limiting amount of a TLR agonist.

A "sample" includes whole blood or a fraction thereof comprising lymphocytes. This method includes micro-arrays, macro-arrays and nano-arrays on planar or spherical solid supports. A micro- or macro-array is useful. A "sample" also includes a small volume sample of from about 0.5 µl to 1000 µl including 5 µl, 10 µl, 50 µl and 100 µl as well as larger volumes such as from 1 ml to about 200 ml such as 1 ml, 2 ml, 5 ml, 10 ml or 20 ml.

A wide range of immunoassay techniques are available as can be seen by reference to U.S. Pat. Nos. 4,016,043, 4,424,279 and 4,018,653.

The following is a description of one type of assay. An unlabeled antibody is immobilized on a solid substrate and the sample to be tested for the immune effector molecules (e.g. a cytokine) brought into contact with the bound molecule. After a suitable period of incubation, for a period of time sufficient to allow formation of an antibody-immune effector molecule complex, a second antibody specific to the effector molecule, labeled with a reporter molecule capable of producing a detectable signal, is then added and incubated, allowing time sufficient for the formation of another complex of antibody-effector-labeled antibody. Any unreacted material is washed away, and the presence of the effector molecule is determined by observation of a signal produced by the reporter molecule. The results may either be qualitative, by simple observation of the visible signal, or may be quantitated by comparing with a control sample containing known amounts of antigen. This generalized technique is well known to those skilled in the art as would be any of a number of variations.

In these assays, a first antibody having specificity for the instant immune effectors is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, spheres, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-120 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the effector molecule. The second antibody is linked to a reporter molecule which is used to indicate the binding of the second antibody to the effector molecule.

There is many variations to this assay. One particularly useful variation is a simultaneous assay where all or many of the components are admixed substantially simultaneously. Furthermore, binding of an antibody to a cytokine may be determined by binding of a labeled antibody directed to the first mentioned antibody.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. Examples of suitable fluorophores are provided in Table 1. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. Again, the present disclosure extends to a substantially simultaneous assay.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. The fluorescent labeled antibody is allowed to bind to the first antibody-antigen complex. After washing off the unbound reagent, the remaining tertiary complex is then exposed to the light of the appropriate wavelength the fluorescence observed indicates the presence of the antigen of interest. Immunofluorescence and enzyme immunoassay techniques are both very well established in the art and are particularly preferred for the present method. However, other reporter molecules, such as radio-isotope, chemiluminescent or bioluminescent molecules, may also be employed.

There are a range of other detection systems which may be employed including colloidal gold and all such detection systems are encompassed by the present disclosure.

The present disclosure also contemplates genetic assays such as involving PCR analysis to detect RNA expression products of a genetic sequence encoding an immune effector.

In one embodiment, PCR is conducted using pairs of primers, one or both of which are generally labeled with the same or a different reporter molecule capable of giving a distinguishable signal. The use of fluorophores is particularly useful in the practice of the present disclosure. Examples of suitable fluorophores may be selected from the list given in Table 1. Other labels include luminescence and phosphorescence as well as infrared dyes. These dyes or fluorophores may also be used as reporter molecules for antibodies.

TABLE 1

List of suitable fluorophores

| Probe | Ex[1] (nm) | Em[2] (nm) |
|---|---|---|
| Reactive and conjugated probes | | |
| Hydroxycoumarin | 325 | 386 |
| Aminocoumarin | 350 | 455 |
| Methoxycoumarin | 360 | 410 |
| Cascade Blue | 375; 400 | 423 |
| Lucifer Yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| APC-Cy7 conjugates | 650; 755 | 767 |
| Red 613 | 480; 565 | 613 |
| Fluorescein | 495 | 519 |
| FluorX | 494 | 520 |
| BODIPY-FL | 503 | 512 |
| TRITC | 547 | 574 |
| X-Rhodamine | 570 | 576 |
| Lissamine Rhodamine B | 570 | 590 |
| PerCP | 490 | 675 |
| Texas Red | 589 | 615 |
| Allophycocyanin (APC) | 650 | 660 |
| TruRed | 490, 675 | 695 |
| Alexa Fluor 350 | 346 | 445 |
| Alexa Fluor 430 | 430 | 545 |
| Alexa Fluor 488 | 494 | 517 |
| Alexa Fluor 532 | 530 | 555 |
| Alexa Fluor 546 | 556 | 573 |
| Alexa Fluor 555 | 556 | 573 |
| Alexa Fluor 568 | 578 | 603 |
| Alexa Fluor 594 | 590 | 617 |
| Alexa Fluor 633 | 621 | 639 |
| Alexa Fluor 647 | 650 | 688 |
| Alexa Fluor 660 | 663 | 690 |
| Alexa Fluor 680 | 679 | 702 |
| Alexa Fluor 700 | 696 | 719 |
| Alexa Fluor 750 | 752 | 779 |
| Cy2 | 489 | 506 |
| Cy3 | (512); 550 | 570; (615) |
| Cy3,5 | 581 | 596; (640) |
| Cy5 | (625); 650 | 670 |
| Cy5,5 | 675 | 694 |
| Cy7 | 743 | 767 |
| Nucleic acid probes | | |
| Hoechst 33342 | 343 | 483 |
| DAPI | 345 | 455 |
| Hoechst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| SYTOX Green | 504 | 523 |
| SYTOX Orange | 547 | 570 |
| Ethidium Bromide | 493 | 620 |
| 7-AAD | 546 | 647 |
| Acridine Orange | 503 | 530/640 |
| TOTO-1, TO-PRO-1 | 509 | 533 |
| Thiazole Orange | 510 | 530 |
| Propidium Iodide (PI) | 536 | 617 |
| TOTO-3, TO-PRO-3 | 642 | 661 |
| LDS 751 | 543; 590 | 712; 607 |
| Fluorescent Proteins | | |
| Y66F | 360 | 508 |
| Y66H | 360 | 442 |
| EBFP | 380 | 440 |

TABLE 1-continued

List of suitable fluorophores

| Probe | Ex[1] (nm) | Em[2] (nm) |
|---|---|---|
| Wild-type | 396, 475 | 50, 503 |
| GFPuv | 385 | 508 |
| ECFP | 434 | 477 |
| Y66W | 436 | 485 |
| S65A | 471 | 504 |
| S65C | 479 | 507 |
| S65L | 484 | 510 |
| S65T | 488 | 511 |
| EGFP | 489 | 508 |
| EYFP | 514 | 527 |
| DsRed | 558 | 583 |
| Other probes | | |
| Monochlorobimane | 380 | 461 |
| Calcein | 496 | 517 |

[1]Ex: Peak excitation wavelength (nm)
[2]Em: Peak emission wavelength (nm)

Any suitable method of analyzing fluorescence emission is encompassed herein. In this regard, techniques taught herein include but are not restricted to 2-photon and 3-photon time resolved fluorescence spectroscopy as, for example, disclosed by Lakowicz et al. (1997) Biophys. J. 72:567, fluorescence lifetime imaging as, for example, disclosed by Eriksson et al. (1993) Biophys. J. 2:64 and fluorescence resonance energy transfer as, for example, disclosed by Youvan et al. (1997) Biotechnology et elia 3:1-18.

Luminescence and phosphorescence may result respectively from a suitable luminescent or phosphorescent label as is known in the art. Any optical means of identifying such label may be used in this regard.

Infrared radiation may result from a suitable infrared dye. Exemplary infrared dyes that may be employed in the present disclosure include but are not limited to those disclosed in Lewis et al. (1999) Dyes Pigm. 42(2):197, Tawa et al. Mater. Res. Soc. Symp. Proc. 488 [Electrical, Optical and Magnetic Properties of Organic Solid-State Materials IV], 885-890, Daneshvar et al (1999) J. Immunol. Methods 226 (1-2):119-128, Rapaport et al. (1999) Appl. Phys. Lett. 74(3):329-331 and Durig et al. (1993) J. Raman Spectrosc. 24(5):281-285. Any suitable infrared spectroscopic method may be employed to interrogate the infrared dye. For instance, fourier transform infrared spectroscopy as, for example, described by Rahman et al. (1998) J. Org. Chem. 63:6196, may be used in this regard.

Suitably, electromagnetic scattering may result from diffraction, reflection, polarization or refraction of the incident electromagnetic radiation including light and X-rays. Such scattering can be used to quantitate the level of mRNA or level of protein.

Flow cytometry is particularly useful in analyzing fluorophore emission.

As is known in the art, flow cytometry is a high throughput technique which involves rapidly analyzing the physical and chemical characteristics of particles (e.g. labeled mRNA, DNA or proteins) as they pass through the path of one or more laser beams while suspended in a fluid stream. As each particle intercepts the laser beam, the scattered light and fluorescent light emitted by each cell or particle is detected and recorded using any suitable tracking algorithm as, for example, described hereunder.

A modern flow cytometer is able to perform these tasks up to 100,000 cells/particles s$^{-1}$. Through the use of an optical array of filters and dichroic mirrors, different wavelengths of fluorescent light can be separated and simultaneously detected. In addition, a number of lasers with different excitation wavelengths may be used. Hence, a variety of fluorophores can be used to target and examine, for example, different immune effectors within a sample or immune effectors from multiple subjects.

Suitable flow cytometers which may be used in the methods of the present disclosure include those which measure five to nine optical parameters (sec Table 2) using a single excitation laser, commonly an argon ion air-cooled laser operating at 15 mW on its 488 nm spectral line. More advanced flow cytometers are capable of using multiple excitation lasers such as a HeNe laser (633 nm) or a HeCd laser (325 nm) in addition to the argon ion laser (488 or 514 nm).

TABLE 2

Exemplary optical parameters which may be measured by a flow cytometer.

| Parameter | Acronym | Detection angle form incident laser beam | Wavelength (nm) |
| --- | --- | --- | --- |
| Forward scattered light | FS | 2-5° | 488* |
| Side scattered light | SS | 90° | 488* |
| "Green" fluorescence | FL1 | 90° | 510-540† |
| "Yellow" fluorescence | FL2 | 90° | 560-580† |
| "Red" fluorescence | FL3 | 90° | >650# |

*using a 488 nm excitation laser
†width of bandpass filter
longpass filter

For example, Biggs et al. (1999) *Cytometry* 36:36-45 have constructed an 11-parameter flow cytometer using three excitation lasers and have demonstrated the use of nine distinguishable fluorophores in addition to forward and side scatter measurements for purposes of immunophenotyping (i.e. classifying) particles. Selection of parameters can be adequately used depends heavily on the extinction coefficients, quantum yields and amount of spectral overlap between all fluorophores (Malemed et al. (1990) *"Flow cytometry and sorting"*, $2^{nd}$ Ed., New York, Wiley-Liss). It will be understood that the present disclosure is not restricted to any particular flow cytometer or any particular set of parameters. In this regard, the disclosure also contemplates use in place of a conventional flow cytometer, a microfabricated flow cytometer as, for example, disclosed by Fu et al. (1999) *Nature Biotechnology* 17:1109-1111.

The assay enabled herein may be automated or semi-automated for high throughput screening or for screening for a number of immune effectors from the one subject. The automation is conveniently controlled by computer software.

The present disclosure further contemplates therefore web-based and non-web-based systems where data on the cell-mediated immunoresponsiveness of a subject are provided by a client server or other architecture platform to a central processor which analyzes and compares to a control and optionally considers other information such as patient age, sex, weight and other medical conditions and then provides a report, such as, for example, a risk factor for disease severity or progression or status or an index of probability of disease development. A business method is, therefore, also provided whereby blood is collected in transportable tubes which is then analyzed for cell-mediated immunoresponsiveness at a defined location and the results then sent in the form of an electronic report via a client server or other architecture platform to a clinical care provider.

Hence, knowledge-based computer software and hardware also form part of the present disclosure. This facilitates clinical care to ascertain whether a disease condition including infection, cancer of inflammation or a medicament or toxicant is inducing or is associated with immunosuppression.

In an embodiment, the assays enabled by the instant disclosure may be used in existing or newly developed knowledge-based architecture or platforms associated with pathology services. For example, results from the assays are transmitted via a communications network (e.g. the Internet) or telephone connection to a processing system in which an algorithm is stored and used to generate a predicted posterior probability value which translates to the index of cell-mediated immunoresponsiveness or immunosuppression which is then forwarded to an end user in the form of a diagnostic or predictive report. This report may also form the basis of clinical care management and personalized medicine.

The assay may, therefore, be in the form of a kit or computer-based system which comprises the reagents necessary to detect the concentration of the immune effector molecule following exposure of lymphocytes to an antigen and a limiting amount of a TLR agonist and the computer hardware and/or software to facilitate determination and transmission of reports to a clinician.

For example, the present disclosure teaches a method of allowing a user to determine the status of cell-mediated immunoresponsiveness of a subject, the method including:

(a) receiving data in the form of levels or concentrations of an immune effector molecule which, relative to a control, provide a correlation as the state of cell-mediated immunoresponsiveness in a subject, via a communications network, the immune effector molecule measured after exposure of lymphocytes to an antigen and a limiting amount of a TLR agonist;

(b) processing the subject data via univariate or multivariate analysis to provide an immunoresponsiveness value;

(c) determining the status of the subject in accordance with the results of the immunoresponsiveness value in comparison with predetermined values; and (d) transferring an indication of the status of the subject to the user via the communications network.

Reference to the "univariate" or "multivariate" analysis includes an algorithm which performs the univariate or multivariate analysis function.

Conveniently, the method generally further includes:

(a) having the user determine the data using a remote end station; and (b) transferring the data from the end station to the base station via the communications network.

The base station can include first and second processing systems, in which case the method can include:

(a) transferring the data to the first processing system:

(b) transferring the data to the second processing system; and (c) causing the first processing system to perform the univariate or multivariate analysis function to generate the cell-mediated immunoresponsiveness value.

The method may also include:

(a) transferring the results of the univariate or multivariate analysis function to the first processing system; and (b) causing the first processing system to determine the status of the subject.

In this case, the method also includes at least one of:

(a) transferring the data between the communications network and the first processing system through a first firewall; and (b) transferring the data between the first and the second processing systems through a second firewall.

The second processing system may be coupled to a database adapted to store predetermined data and/or the univariate or multivariate analysis function, the method including:

(a) querying the database to obtain at least selected predetermined data or access to the univariate or multivariate analysis function from the database; and (b) comparing the selected predetermined data to the subject data or generating a predicted probability index of a level of cellular immunoresponsiveness or immunosuppression.

The second processing system can be coupled to a database, the method including storing the data in the database.

The method can also include causing the base station to:

(a) determine payment information, the payment information representing the provision of payment by the user; and (b) perform the comparison in response to the determination of the payment information.

The present disclosure also provides a base station for determining the status of a subject with respect to cell-mediated immunoresponsiveness or immunosuppression, the base station including:

(a) a store method;

(b) a processing system, the processing system being adapted to:

(c) receive subject data from the user viu a communications network, the data including levels of immune effector molecule wherein the level of the effector molecule relative to a control provides a correlation to the state of cell-mediated immunoresponsiveness wherein the immune effector molecule is determined after exposure of lymphocytes to an antigen and a limiting amount of a TLR agonist;

(d) performing an algorithmic function including comparing the data to predetermined data;

(e) determining the status of the subject in accordance with the results of the algorithmic function including the comparison; and (c) output an indication of the status of the subject to the user via the communications network.

The processing system can be adapted to receive data from a remote end station adapted to determine the data.

The processing system may include:

(a) a first processing system adapted to:

(i) receive the data; and (ii) determine the status of the subject in accordance with the results of the univariate or multivariate analysis function including comparing the data: and (b) a second processing system adapted to:

(i) receive the data from the processing system;

(ii) perform the univariate or multivariate analysis function including the comparison; and (iii) transfer, the results to the first processing system.

The processing system can be coupled to a database, the processing system being adapted to store the data in the database.

In accordance with this embodiment, levels of the immune effector molecule may be screened alone or in combination with other biomarkers or disease indicators. An "altered" level means an increase or elevation or a decrease or reduction in the concentrations of the immune effector molecule.

The determination of the concentrations or levels of the immune effector molecule enables establishment of a diagnostic rule based on the concentrations relative to controls. Alternatively, the diagnostic rule is based on the application of a statistical and machine learning algorithm. Such an algorithm uses relationships between effector molecule and disease status observed in training data (with known disease or cell-mediated immunoresponsiveness status) to infer relationships which are then used to predict the status of subjects with unknown status. An algorithm can be employed which provides an index of probability that a subject has a certain level of cell-mediated immunoresponsiveness and/or a disease condition. The algorithm performs a univariate or multivariate analysis function.

Hence, the present disclosure provides a diagnostic rule based on the application of statistical and machine learning algorithms. Such an algorithm uses the relationships between immune effector molecule and level of cell-mediated immunoresponsiveness or immunosuppression observed in training data (with known immune status) to infer relationships which are then used to predict the status of patients with unknown immune status. Practitioners skilled in the art of data analysis recognize that many different forms of inferring relationships in the training data may be used without materially changing the present disclosure.

The present disclosure further contemplates the use of a knowledge base of training data comprising levels of immune effector molecule from a subject with a known cell-mediated immunoresponsiveness level to generate an algorithm which, upon input of a second knowledge base of data comprising levels of the same immune effector molecule from a subject with an unknown immunoresponsiveness level, provides an index of probability that predicts the nature of the cell-mediated immunoresponsiveness.

The term "training data" includes knowledge of levels of immune effector molecule relative to a control wherein the immune effector molecule is determined after exposure of lymphocytes an antigen and a limiting amount of adaptive one or more agents which potentiate the innate and/or adaptive immune system. A "control" includes a comparison to levels of immune effector molecule in a subject with "normal" immunoresponsiveness or may be a statistically determined level based on trials.

Hence, the term "training data" includes levels of an immune effector molecule.

The levels or concentrations of the immune effector molecule provide the input test data referred to herein as a "second knowledge base of data". The second knowledge base of data either is considered relative to a control or is fed into an algorithm generated by a "first knowledge base of data" which comprise information of the levels of an immune effector in a subject with a known immunological status. The second knowledge base of data is from a subject of unknown status with respect to cell mediated immunoresponsiveness. The output of the algorithm or the comparison to a control is a probability or risk factor, referred to herein as "an index of probability", of a subject having a certain level of immunoresponsiveness or immunosuppressive.

Data generated from the levels of immune effector molecule are input data. The input of data comprising the immune effector levels is compared with a control or is put into the algorithm which provides a risk value of the likelihood that the subject has, for example, an immunosuppressive condition. A treatment regime can also be monitored to ascertain the presence of any immunosuppression. A level of immunosuppression may increase the risk of a subject getting a secondary infection or having a relapse (e.g. during cancer therapy or treatment of a pathogenic infection).

As described above, methods for diagnosing an immunoresponsiveness or immunosuppressive condition by determining the extent to which a subject can mount an innate and/or adaptive immune response via a level of an immune effector molecule provides a second knowledge base data in an algorithm generated with first knowledge base data or levels of the same effector molecule in subjects with a known immune status. Also provided are methods of detecting immunoresponsiveness comprising determining the presence and/or velocity of an immune effector molecule following stimulation of the innate and/or adaptive immune system in a subject's sample. By "velocity" it is meant the change in the concentration of the effector molecule in a subject's sample over time.

As indicated above, the term "sample" as used herein means any sample containing one or more lymphocytes including, but not limited to, whole blood, a whole blood fraction, tissue extracts and freshly harvested cells.

The method of the subject disclosure may be used in the diagnosis and staging of a disease. The present disclosure may also be used to monitor the progression of a condition and to monitor whether a particular treatment is effective or not. In particular, the method can be used to monitor immunosuppression following surgery, cancer therapy or other or medication or exposure to toxicants.

In an embodiment, the subject disclosure contemplates a method for monitoring for immunosuppression in a subject, comprising:
  (a) providing a sample from a subject;
  (b) determining the level of an immune effector molecule following stimulation by an antigen and a limiting amount of a TLR agonist;
wherein the level of the immune effector relative to a control provides a correlation to the state of cell-mediated immunoresponsiveness and subjecting the levels to an algorithm to provide an index of probability of the subject having a certain level of immunoresponsiveness; and
  (c) repeating steps (a) and (b) at a later point in time and comparing the result of step (b) with the result of step (c) wherein a difference in the index of probability is indicative of the progression of the condition in the subject.

Reference to an "algorithm" or "algorithmic functions" as outlined above includes the performance of a univariate or multivariate analysis function. A range of different architectures and platforms may be implemented in addition to those described above. It will be appreciated that any form of architecture suitable for implementing the present disclosure may be used. However, one beneficial technique is the use of distributed architectures. In particular, a number of end stations may be provided at respective geographical locations. This can increase the efficiency of the system by reducing data bandwidth costs and requirements, as well as ensuring that if one base station becomes congested or a fault occurs, other end stations could take over. This also allows load sharing or the like, to ensure access to the system is available at all times.

In this case, it would be necessary to ensure that the base station contains the same information and signature such that different end stations can be used.

It will also be appreciated that in one example, the end stations can be hand-held devices, such as PDAs, mobile phones, or the like, which are capable of transferring the subject data to the base station via a communications network such as the Internet, and receiving the reports.

In the above aspects, the term "data" means the levels or concentrations of the immune effector following stimulation by an antigen in the presence of a limiting amount of a TLR agonist. The "communications network" includes the internet and mobile telephone network and telephone land line. When a server is used, it is generally a client server or more particularly a simple object application protocol (SOAP).

One aspect of the present disclosure includes experiments that demonstrate the cell-mediated immune responsiveness of a subject by measuring responsiveness to an antigen in the presence of a limiting amount of TLR agonist. In an embodiment, one or more samples such as a sample of peripheral blood, of enriched white cell fraction of blood or bronchoalveolar lavage may be obtained from a subject having or suspected of development of a particular disease (e.g. autoimmune disease, infection to a pathogenic agent or exposure to beryllium) and the immune responsiveness measured by determination of effector molecules from effector T-cells (e.g. $CD4^+$ T-cells). The assay is conducted in the presence of an antigen and a limiting amount of a TLR agonist.

The immunobinding methods include methods for detecting or quantifying the amount of a reactive component in a sample, which methods require the detection or quantitation of any immune complexes formed during the binding process. Here, one would obtain a sample suspected of containing a cytokine following stimulation of lymphocytes by an antigen in the presence of a limiting amount of TLR agonist and contacting the sample with an antibody and then detecting or quantifying the amount of immune complexes formed under the specific conditions.

Contacting the chosen biological sample with the antibody under conditions effective and for a period of time sufficient to allow the formation of immune complexes (primary immune complexes) is generally a matter of adding the composition to the sample and incubating the mixture for a period of time long enough for the antibodies to form immune complexes with, i.e. to bind to, any effector molecules present. After this time, the sample-antibody composition, such as a tissue section, ELISA plate, ELISpot, dot blot or Western blot, will generally be washed to remove any non-specifically bound antibody species, allowing only those antibodies specifically bound within the primary immune complexes to be detected.

In a particular embodiment, the present disclosure teaches a method for detecting the presence, absence, level or stage of a disease or condition in a human subject, the method comprising contacting whole blood, which comprises at least 10% of the total volume in a reaction mixture, with an antigen and a limiting amount of TLR agonist and measuring the presence or elevation in the level of an immune effector molecule from cells wherein the presence or level of the immune effector molecule is indicative of the disease or condition.

In a further embodiment, the present disclosure enables kits for use with the methods described above. In one embodiment, an immunodetection kit is contemplated. In another embodiment, a kit for analysis of a sample from a subject having or suspected of developing a metal or chemically-induced disease is contemplated. In a more particular embodiment, a kit for analysis of a sample from a subject having or suspected of developing a disease is contemplated. In an embodiment, a kit is for assessing the cell-mediated immune responsiveness of a subject before or after a disease state has developed or before or after a subject is given a medicament or is exposed to a toxicant or pollutant. If an antigen is also employed, the kit may also comprise a particular antigen.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of antigen or effector molecule, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of any of the kits generally includes at least one vial, test tube, flask, bottle, syringe or other container means, into which the testing agent, the antibody or antigen may be placed, and generally, suitably aliquoted. Where a second or third binding ligand or additional component is provided, the kit will also generally contain a second, third or other additional container into which this ligand or component may be placed. The kits taught by the present disclosure also typically include a means for containing the antibody, antigen, and any other reagent containers in close confinement for commercial sale. Such containers may include injection or blow-molded plastic containers into which the desired vials are retained.

Also contemplated herein is an improved assay to detect a cell-mediated immune response or the level thereof in a subject, the assay comprising incubating lymphocytes from the subject with an antigen and detecting for the presence of or elevation in effector molecules, the improvement comprising further incubating the lymphocytes with a limiting amount of a TLR agonist.

The present disclosure further provides a method of treatment of a subject having a pathogenic infection, an autoimmune disorder or cancer or a propensity for developing such a condition or disorder, the method comprising contacting a source of lymphocytes from the subject with an antigen and a limiting amount of TLR agonist and measuring the presence or elevation in the level of an immune effector molecule from T-cells wherein the presence or level of the immune effector molecule is indicative of the level of cell-mediated responsiveness of the subject which is indicative of the presence, absence, level or state of the condition or disorder and then treating the condition or disorder.

Reference herein to a "TLR agonist" includes a TLR-7/8 agonist such as R848.

Aspects taught therein are further described by the following non-limiting Examples.

Example 1

Development of Assay

Heparinized blood samples are collected into a vacuum tube (Li-Hep Vacuette [Registered Trade Mark] tubes (Greiner Bio-one, Germany)).

Aliquots of the blood samples were incubated with various concentrations of Toll-like receptor agonists: Imidazoquinoline compound—TLR-7/8 ligand, R848 (GL Synthesis, Inc.), Lipomannan TLR-2 ligand (InvivoGen. San Diego), Pam3CSK4 TLR-2 ligand (InvivoGen, San Diego), Poly (I:C) TLR-3 ligand (InvivoGen, San Diego). Lipopolysaccharide TLR-4 ligand (Sigma, Australia), and CpG oligodeoxynucleotides TLR-9 ligand (Hycult Biotechnology, Netherlands); or T-cell receptor agonists: phytohemagglutinin (Cellistis Limited, Australia) anti-human CD3ε antibody (mouse $IgG_1$ clone UCHT1; eBioscience, San Diego), and antibodies to T-cell receptor complex: or saline control in a number of different sized blood collection tubes recommended by the manufacturers of the human QFT test (Cellestis Limited, Australia). T-cell receptor-independent stimulants include phorbol myristate acetate (PMA), concanavalnA (ConA) and pokeweek mitogen. Aliquots may be small volumes such as 1 μl to 1000 μl or larger volumes such as 0.5 ml to 200 ml.

In some experiments, glucose is added at various concentrations to the blood before initiation of incubation.

Stimulated blood samples were incubated for 1 to 48 hours including 16-24 hours in the presence of antigen and a limiting amount of a TLR agonist at 37° C., after which plasma was harvested from above the settled blood cells. The amount of IFN-γ present in each plasma sample was then quantified using the QFT ELISA (Cellestis Limited. Australia) as per the manufacturer's instructions. Sample IFN-γ was alternatively quantified using the more sensitive QFT-TB Gold ELISA (Cellestis Limited, Australia) as per the manufacturer's instructions.

ELISA optical density values for IFN-γ standards run on each ELISA plate were used to construct a standard curve from which the amount of IFN-γ present in each of the test plasma samples was converted to IU/mL, values.

In an embodiment, 1 ml aliquots of the blood samples were incubated with various concentrations of R848 (GL Synthesis Inc.) in QFT-Nil tubes Cellestis Ltd. Australia, either as supplied or spiked with a peptide set covering the Epstein-Barr virus (EBV) EBNA1 protein (JPT Peptide Technologies) or in CMV tubes (QFT-CMV, Cellesits Ltd, Australia).

Example 2

Background Responses to R848 in QFT-Nil Tubes

Various concentrations of R848 were added to 1 ml of whole blood in QFT-Nil tubes. Blood was incubated at 37° C. for 16-24 hours before the tubes were centrifuged and the IFNγ concentration of the plasma determined by ELISA (IU/ml). FIG. 1 and Table 3 show the background responses to various concentrations of R848, with mean and SEM values plotted for each concentration.

TABLE 3

| | \multicolumn{7}{c}{R848 Concentration} | | | | | | |
|---|---|---|---|---|---|---|---|
| | 0.01 µg/ml | 0.02 µg/ml | 0.025 µg/ml | 0.03 µg/ml | 0.04 µg/ml | 0.05 µg/ml | 0.1 µg/ml |
| Number of values | 31 | 16 | 5 | 16 | 16 | 44 | 15 |
| Mean | −0.009677 | 0.0100 | 0.0330 | 0.0925 | 0.5144 | 1.084 | 21.58 |
| Std. Deviation | 0.03060 | 0.05680 | 0.04894 | 0.2248 | 1.275 | 1.908 | 37.57 |
| Std. Error | 0.005497 | 0.01420 | 0.02189 | 0.05621 | 0.3188 | 0.2877 | 9.701 |

This example demonstrates that below 0.05 µg/ml R848, background responses to R848 alone is not significant in QFT-Nil tubes. When 0.1 µg/ml R848 is added to QFT-Nil tubes, there are significant background responses seen in many donors.

Example 3

Boosting Responses to Antigens Upon the Addition of R848 to QFT Tubes

Figure 2:
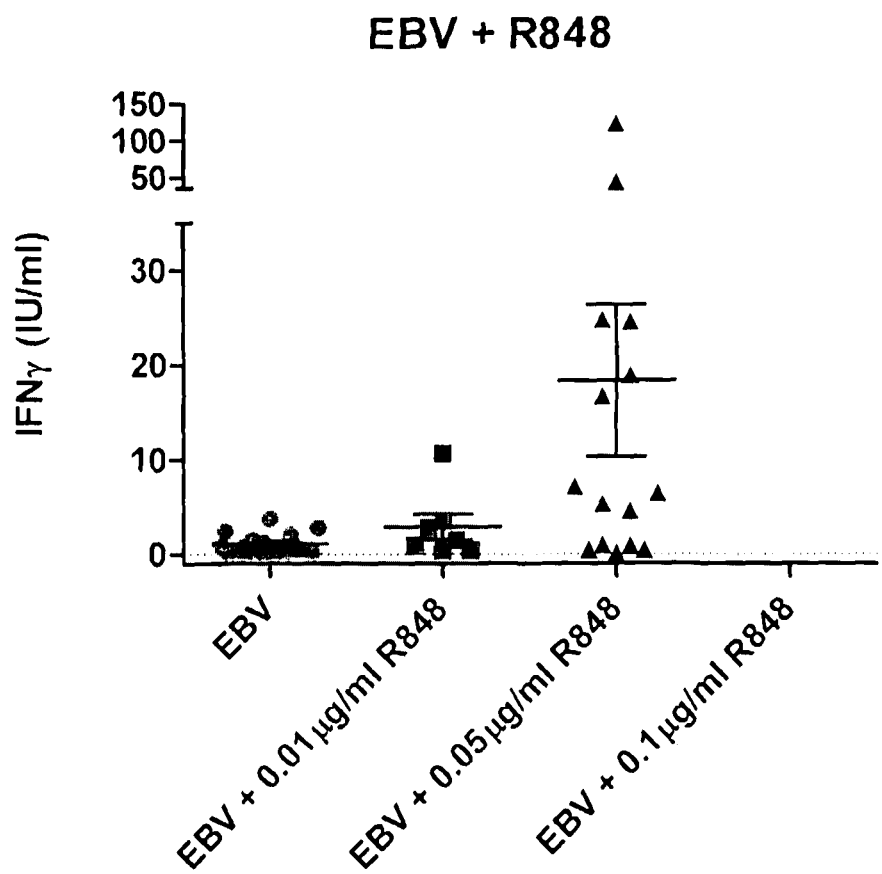
FIG. 2 is a graphical representation of IFN-γ responses from whole blood cultures exposed to 0.5 µg/ml Epstein-Barr virus (EBV) and differing concentrations of R848 (0.01 µg/ml, 0.05 µg/ml and 0.1 µg/ml).
Figure 3:
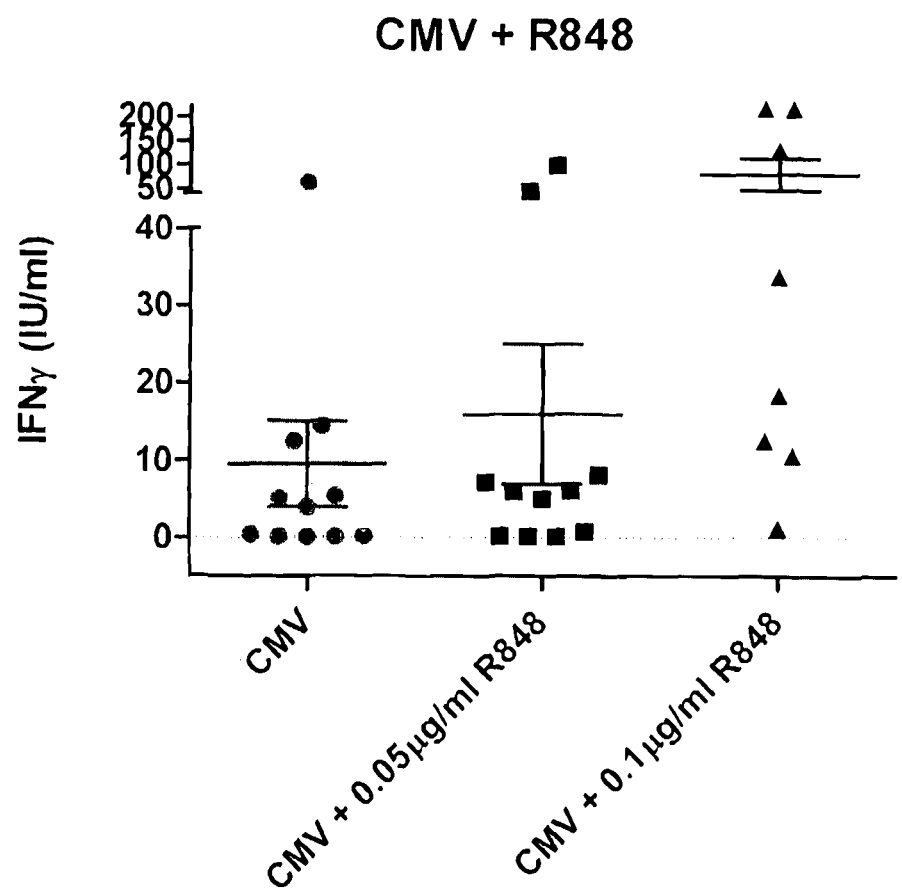
FIG. 3 is a graphical representation of IFN-γ responses from whole blood cultures exposed to 0.5 μg/ml cytomegalovirus (CMV) and differing concentrations of R848 (0.05 μg/ml and 0.1 μg/ml).

Various concentrations of R848 were added to 1 ml of whole blood in either QFT-Nil tubes containing 0.5 µg/ml EBV EBNA 1 pepMix or QFT-CMV tubes. Blood was incubated at 37° C. for 16-24 hours before the tubes were centrifuged and the IFNγ concentration of the plasma determined by ELISA (presented as IU/ml). FIG. 2 and Table 4 (EBV+R848) and FIG. 3 (CMV+R848) and Table 5, show the individual values for each donor, calculated as the response to the combination of antigen+R848. minus the background responses to the same concentration of R848 alone. Therefore, these graphs depict the boost in the antigen responses seen upon the addition of R848. Data points for individual donors are marked, as well as the mean and Standard Error of the mean for each concentration data set.

TABLE 4

| | \multicolumn{4}{c}{EBV + R848} | | | |
|---|---|---|---|---|
| | EBV | EBV + 0.01 µg/ml R848 | EBV + 0.05 µg/ml R848 | EBV + 0.1 µg/ml R848 |
| Number of values | 15 | 7 | 15 | 15 |
| Mean | 1.080 | 2.857 | 18.32 | 29.57 |
| Std. Deviation | 1.132 | 3.621 | 31.05 | 37.03 |
| Std. Error | 0.2923 | 1.369 | 8.017 | 9.562 |

TABLE 5

| | \multicolumn{3}{c}{CMV + R848} | | |
|---|---|---|---|
| | CMV | CMV + 0.05 µg/ml R848 | CMV + 0.1 µg/ml R848 |
| Number of values | 11 | 11 | 8 |
| Mean | 9.496 | 15.96 | 79.53 |
| Std. Deviation | 18.34 | 29.91 | 92.84 |
| Std. Error | 5.530 | 9.018 | 32.82 |

These experiments show that responses to both the EBV EBNA1 peptide pool and the QFT-CMV peptides can be boosted in the presence of R848. For the EBV responses, there is a significant boost in when 0.05 µg/ml R848 is added. In the QFT-CMV tubes, the boost in responses when 0.05 µg/ml R848 is added is not as large as that seen for EBV. However, the boost when 0.1 µg/ml R848 is added is much greater.

In conclusion, responses to the antigen-R848 combined stimuli are greater than that seen by adding together the responses to the antigen and R848 alone individually.

Example 4

Clinical Study Using R848 to Augment QFT-TB Response in TB Suspects and Patients R848 was tested as a stimulant in a QFT-TB tube as part of a clinical study. Patients with active TB disease (confirmed by culture), patients suspected of having TB and their household contacts (HHC) were recruited for this study. In addition to the standard QFT-TB gold in tube, two additional tests were employed with the addition of two different concentrations of R848 (0.05 µg/ml and 0.01 µg/ml), both alone in QFT-Nil tubes and in combination with the current QFT-TB tube.

Patient data are provided in Table 6.

TABLE 6

| \multicolumn{2}{c}{Patient Information} | |
|---|---|
| Subject | Number |
| Confirmed TB | 14 |
| Suspected TB | 8 |
| HHC | 11 |
| QFN positive | 30 |
| QFN negative | 3 |
| Total | 33 |
| Total evaluated | 26* |

Figure 4:
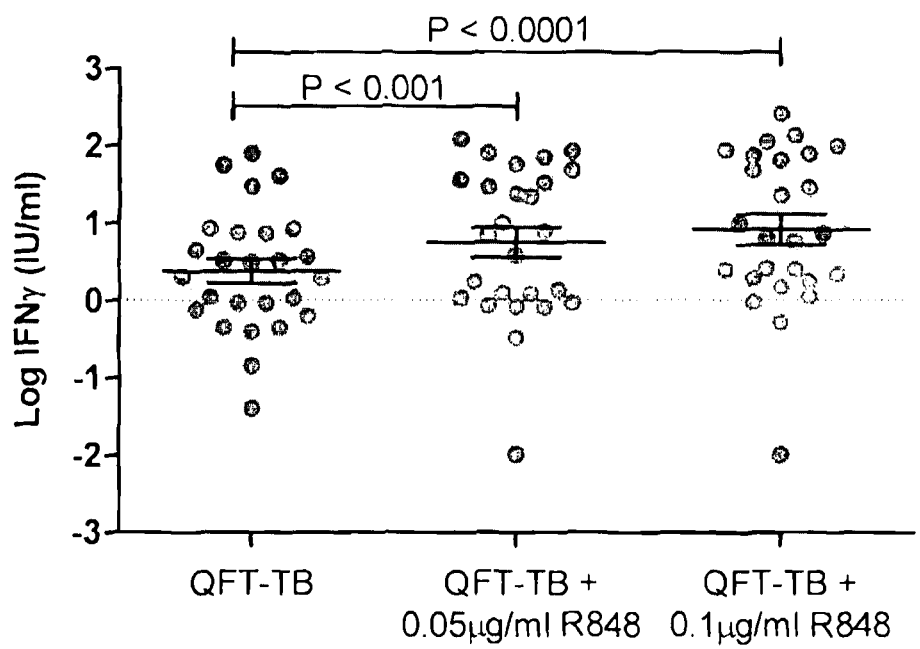
FIG. 4 is a graphical representation of IFN-γ responses from whole blood cultures from patients suspected of having tuberculosis or their household contacts using the QFT in the presence of 0.05 μg/ml or 0.1 μg/ml R848. Each data point represents the response minus the respective background (Nil; Nil+0.05 μg/ml R848: and N+0.1 μg/ml R848, respectively). Data were log-transformed and analyzed by repeated measures ANOVA with a Bonferronipost test. Bars indicate the mean value with SEM.

(*6 patients did not have completed data sets and were excluded from the analysis)

the addition of R848 at 0.05 µg/ml and 0.1 µg/ml significantly enhanced the QFT-TB response in subjects demonstrating a positive response to the QFT-TB test alone (P<0.001 and P<0.0001, respectively) [FIG. 4].

Two of the patients who tested negative with the current QFT-TB tube became positive when R848 was added to the tube (at both concentrations tested). Both these patients were TB suspects.

Those skilled in the art will appreciate that aspects of the subject matter described. It is to be understood that the disclosure encompasses all such variations and modifications. The disclosure also includes all of the steps, features, compositions and compounds referred to or indicated in this specification, individually or collectively, and any and all combinations of any two or more of the steps or features.

BIBLIOGRAPHY

Biggs et al (1999) *Cytometry* 36:36-45
Daneshvar et al. (1999) *J. Immunol. Methods* 226 (1-2):119-128
Durig et al. (1993) *J. Raman Spectrosc.* 24(5):281-285
Eriksson et al. (1993) *Biophys. J.* 2:64

Fu et al. (1999) *Nature Biotechnology* 17:1109-1111
Hemmi et al. (2002) *Nature Immunology* 3:196-200
Lakowicz et al. (1997) *Biophys. J.* 72:567
Lewis et al. (1999) *Dyes Pigm.* 42(2):197
Malemed et al. (1990) "Flow cytometry and sorting", 2$^{nd}$ Ed., New York, Wiley-Liss
Nowroozalizadeh et al. (2009) *Cytokine* 46:325-31
Peel et al. (1985) *J Med Chem* 28:298-302
Petkovic-Duran et al. (2009) *Biotechniques* 47:827-834
Rahman et al. (1998) *J. Org. Chem.* 63:6196
Rapaport et al. (1999) *Appl. Phys. Lett.* 74(3):329-331
Tawa et al, *Mater. Res. Soc. Symp. Proc.* 488 [Electrical, Optical and Magnetic Properties of Organic Solid-State Materials IV], 885-890
Youvan et al. (1997) *Biotechnology et elia* 3: 1-18

The invention claimed is:

1. A method for measuring in vitro immune responsiveness to an antigen by lymphocytes from a test subject that is suspected of having been previously exposed to the antigen, comprising:
   (A) incubating in vitro
      (i) a sample that comprises lymphocytes from the test subject, with
      (ii) one or more antigens associated with a disease or condition suspected of being present in the test subject, and
      (iii) a limiting amount of a Toll-like receptor (TLR) agonist wherein the TLR agonist is selected from the group consisting of R848 (imidazoquinoline), lipomannan, and poly (I:C), said limiting amount of the TLR agonist being determined by a method that comprises a step selected from:
         (a) identifying an amount of the TLR agonist that stimulates the lymphocytes to produce no background response or a minimal background response when incubated with no antigen present and thereby determining the limiting amount, and
         (b) identifying an amount of the TLR agonist such that the TLR agonist is present at a ratio of TLR agonist to said one or more antigens of from 1:500 to 1:1.5 and thereby determining the limiting amount,
   wherein said step of incubating the sample, the one or more antigens, and the limiting amount of TLR agonist is for a time and under conditions sufficient for:
      (1) antigen responsiveness, by one or more T cells that are present in said lymphocytes, to one or more of said one or more antigens, thereby to stimulate the lymphocytes to produce an effector molecule, and
      (2) TLR agonist responsiveness, by one or more T cells that are present in said lymphocytes, to said limiting amount of the TLR agonist to stimulate the lymphocytes to produce an enhanced level of the effector molecule when the limiting amount of the TLR agonist and said one or more antigens are present, relative to the level of the effector molecule that is produced when the TLR agonist is absent; and
   (B) detecting the enhanced level of the effector molecule that is produced by the lymphocytes stimulated according to step (A), wherein the detected enhanced level of the effector molecule is greater than a detectable effector molecule level that is a sum of (i) the detectable effector molecule level that can be produced by said lymphocytes incubated only with said one or more antigens, plus (ii) the detectable effector molecule that can be produced by said lymphocytes incubated only with said limiting amount of the TLR agonist, wherein if the enhanced level of the effector molecule that is detected is higher than a control level of the effector molecule that is detected following incubation of control lymphocytes from a healthy control subject with the limiting amount of the TLR agonist and the one more antigens, then the enhanced level indicates that the lymphocytes from the test subject have been previously exposed to the antigen associated with the disease or condition suspected of being present in the test subject, and wherein the effector molecule is selected from IFN-γ, TNF-α, IL-2, IL-4, IL-6, IL-6 (CXCL8), IL-10, IL-12, IL-13, IL-16 (LCF), IL-17, IL-1α(IL-1F1), IL-1β(IL-1F2), IL-1rα (IL-1F3), TGF-β, G-CSF, GM-CSF, complement component 5a (C5a), Groα (CXCL1), sICAM-1 (CD54), IP-10 (CXCL10), I-TAC (CXCL11), MCP-1 (CCL2), MIF (GIF), MIP-1α(CCL3), MIP-1β(CCL4), RANTES (CCL5) and MIG (CXCL9).

2. The method of claim 1 wherein the TLR agonist is R848.

3. The method of claim 1 wherein the test subject is a human.

4. The method of claim 1 wherein the sample is undiluted whole blood.

5. The method of claim 4 wherein the whole blood is collected in a tube comprising heparin.

6. The method of claim 1 wherein the effector molecule is interferon-γ (IFN-γ).

7. The method of claim 1 wherein the effector molecule is detected with antibodies specific for the effector molecule.

8. The method of claim 1 wherein the test subject has or has previously been exposed to an infection by a pathogenic agent selected from the group consisting of *Mycobacterium* species, *Staphylococcus* species, *Streptococcus* species, *Borrelia* species, *Escherichia coli*, *Salmonella* species, *Clostridium* species, *Shigella* species, *Proteus* species, *Bacillus* species, Herpes virus, Hepatitis B or C virus and Human immune deficiency virus (HIV).

9. The method of claim 8 wherein the test subject has or has previously been exposed to an infection by *Mycobacterium tuberculosis*.

10. The method of claim 1 wherein the subject has a disease condition selected from the group consisting of alopecia areata, ankylosing spondylitis, antiphospholipid syndrome, autoimmune Addison's disease multiple sclerosis, autoimmune disease of the adrenal gland, autoimmune hemolytic anemia, autoimmune hepatitis, autoimmune oophoritis and orchitis, Behcet's disease, bullous pemphigoid, cardiomyopathy, celiac sprue-dermatitis, chronic fatigue syndrome (CFIDS), chronic inflammatory demyelinating, chronic inflammatory polyneuropathy, Churg-Strauss syndrome, cicatricial pemphigoid, crest syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), lichen planus, lupus, Meniere's disease, mixed connective tissue disease, multiple sclerosis, myasthenia gravis, myocarditis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arrtritis, sarcoidosis, scleroderma, Sjogren's syndrome, stiff-man syndrome, systemic lupus erythematosus, Takayasu arteritis, temporal arteritis/giant cell arteritis, ulcerative colitis, uveitis, vasculitis, vitiligo and inflammatory bowel disease.

11. The method of claim 10 wherein the disease is Celiac's disease.

12. The method of claim 1 wherein the subject has a cancer selected from the group consisting of ABL1 proto-oncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor.

13. The method of claim 1 wherein the subject was exposed to a toxicant.

14. A method for measuring in vitro immune responsiveness to an antigen by lymphocytes from a test subject that is suspected of having been previously exposed to the antigen, comprising:
(A) incubating in vitro
  (i) a sample that comprises lymphocytes from the test subject, with
  (ii) one or more antigens associated with a disease or condition suspected of being present in the test subject wherein the antigen is selected from an Epstein-Barr Virus (EBV) antigen, a cytomegalovirus (CMV) antigen, and a tuberculosis (TB) antigen, and
  (iii) a limiting amount of a Toll-like receptor (TLR) agonist wherein the TLR agonist is selected from the group consisting of R848 (imidazoquinoline), lipomannan, and poly (I:C), said limiting amount of the TLR agonist being determined by a method that comprises a step selected from:
    (a) identifying an amount of the TLR agonist that stimulates the lymphocytes to produce no background response or a minimal background response when incubated with no antigen present and thereby determining the limiting amount, and
    (b) identifying an amount of the TLR agonist such that the TLR agonist is present at a ratio of TLR agonist to said one or more antigens of from 1:500 to 1:1.5 and thereby determining the limiting amount,
wherein said step of incubating the sample, the one or more antigens, and the limiting amount of TLR agonist is for a time and under conditions sufficient for:
  (1) antigen responsiveness, by one or more T cells that are present in said lymphocytes, to one or more of said one or more antigens, thereby to stimulate the lymphocytes to produce an effector molecule, and
  (2) TLR agonist responsiveness, by one or more T cells that are present in said lymphocytes, to said limiting amount of the TLR agonist to stimulate the lymphocytes to produce an enhanced level of the effector molecule when the limiting amount of the TLR agonist and said one or more antigens are present, relative to the level of the effector molecule that is produced when the TLR agonist is absent; and
(B) detecting the enhanced level of the effector molecule that is produced by the lymphocytes stimulated according to step (A), wherein the detected enhanced level of the effector molecule is greater than a detectable effector molecule level that is a sum of (i) the detectable effector molecule level that can be produced by said lymphocytes incubated only with said one or more antigens, plus (ii) the detectable effector molecule that can be produced by said lymphocytes incubated only with said limiting amount of the TLR agonist,
wherein if the enhanced level of the effector molecule that is detected is higher than a control level of the effector molecule that is detected following incubation of control lymphocytes from a healthy control subject with the limiting amount of the TLR agonist and the one more antigens, then the enhanced level indicates that the lymphocytes from the test subject have been previously exposed to the antigen associated with the disease or condition suspected of being present in the test subject, and wherein the effector molecule is interferon-gamma (IFN-γ).

* * * * *